United States Patent [19]

Frey et al.

[11] Patent Number: 5,600,443
[45] Date of Patent: Feb. 4, 1997

[54] METHOD OF DETERMINING THE AGE OF INK HAVING TIME DEPENDENT CHARACTERISTICS

[75] Inventors: Thomas H. Frey, Agoura Hills; Isaiah Lieberman, Los Angeles, both of Calif.

[73] Assignee: Signa Scan, Inc., Anaheim, Calif.

[21] Appl. No.: 504,892

[22] Filed: Jul. 20, 1995

[51] Int. Cl.$^6$ .................................. G01J 3/427; G01J 3/50
[52] U.S. Cl. ........................ 356/402; 356/71; 356/425; 356/300; 250/226
[58] Field of Search ............................. 356/71, 402, 408, 356/425, 300; 250/226

[56] References Cited

PUBLICATIONS

Cantu, Analytical Chemistry, vol. 63, No. 17, Sep. 1, 1991, pp. 847A–854A.

Primary Examiner—F. L. Evans
Attorney, Agent, or Firm—Morland C. Fischer

[57] ABSTRACT

A method and ink composition are disclosed that utilize two mechanisms for the purpose of indicating the approximate age of an ink that has been deposited on a writing surface. The first mechanism relates to detecting color shifts of pH sensitive compounds in the ink as the result of the evaporation of certain acidic or basic chemicals thereof. The second mechanism relates to the oxidation of compounds in the ink. Spectroscopically generated curves are plotted as the ratio of reactants to products, versus time. The spectral characteristics of the ink are determined in units of percent reflectance of the active compounds in the ink so that the age of the ink can be computed by reference to known reaction rates. A plurality of dyes having differing reaction rates may be added to the ink to enable precise measurements to be made over different time intervals.

4 Claims, 6 Drawing Sheets

METHOD OF DETERMINING THE AGE OF INK HAVING TIME DEPENDENT CHARACTERISTICS

BACKGROUND OF THE INVENTION

1. Field of the Invention

The present invention relates to an ink and to a method for measuring the age of the ink that has been deposited on a writing surface, and is particularly adapted for analyzing signatures and writings to determine the age of the signature or writing and the age of the signature or writing relative to other signatures or writings. The present invention is particularly applicable to investigations that are intended to combat fraud, including medical fraud, insurance fraud, and fraud involving other time dated documents such as wills, trusts, deeds and legal agreements.

2. Background Art

The aging of ink is an important factor in the forensic examination of documents. The ability to accurately time date writings and signatures deposited on a document, or set of documents, can help determine the authenticity of the document or documents and detect fraud, such as, for example, where a document contains several time dated entries which indicate a long span of time, but the writer falsified the document by making the entries all at one time or at a fewer number of sittings than indicated by the dates written on the document.

Aging characteristics of ink are described in a book by R. L. Brunelle and R. W. Reed, entitled *Forensic Examination of Ink and Paper,* which is published by C. C. Thomas of Springfield, Ill. The age of ink deposited on a document may be detected by spectroscopy, as suggested by V. A. Fassel et. al. in their book entitled *Analysis and Application of Rare Earth Materials,* Oslo-Bergen, Tromso, Universitets Forlaget, 1973. In this regard, time dating an ink is dependent upon the composition of the ink and may be determined through analysis such as solvent extraction and spectroscopy.

However, time dating analysis based upon conventional ink compositions has been found to yield inaccurate results, whereby such results are not accepted with a large degree of confidence. In fact, no conventional ink is known having a composition which lends itself to an accurate time dating method.

One of the most common techniques of falsifying documents and perpetrating document fraud is the act of entering multiple time dated entries at one sitting, rather than at successive times. This act constitutes fraud if the entries were made in fewer sittings than indicated by the dates written on the document. By way of example, a patient undergoing treatment requiring different office visits over a period of time is supposed to sign his name on a dated treatment log (known as a sign-in-sheet) each time he is treated. However, the patient may actually sign his name on several lines, containing different dates, all at the same time. The patient or doctor may then submit the falsified treatment record to an insurance company seeking reimbursement for treatments that were never offered or received. This type of fraud is amplified by the pain and suffering multiple which is usually paid by the insurance company based on the costs incurred in medical treatments (typically three to four times medical costs).

In some cases, an entire dated treatment log, covering several months of treatment which was never received, is filled out in one sitting and submitted to an insurance company for payment. The significant costs of this type of fraud are borne ultimately by the insurance company, government agencies and consumers, alike.

Combatting such fraudulent activities is difficult, because the signatures or writings are authentic as to the author, and this information in and of itself offers no proof as to when the writings were actually made. Other problems which complicate the determination of this type of fraud is the fact that no reliable and cost effective technique has been available to accurately identify the age of a deposited ink. Therefore there has been no quick and reliable way to determine whether a person signed or wrote a document at the particular date or dates indicated on the document.

What is therefore needed is a method which will make it possible to not only tell the age of an ink writing but also to distinguish the relative ages of sequential ink writings entered on a document or series of documents over time. What is also needed is one or more chemicals having known, predictable time variable characteristics to be added to an ink in order to cause the ink to change with time after its deposition on a writing surface.

SUMMARY OF THE INVENTION

A first embodiment of the present invention relates to the detection of pH shifts of chemical compounds in the ink. pH shifts will change the composition of the ink by promoting a chemical reaction. Such pH shifts are the result of the evaporation of certain chemicals in the ink. Time dating is achieved by depositing the ink on a writing surface and exposing the ink to the ambient atmosphere so that a pH shift can be detected as the composition of the ink changes with time.

If compound A in the ink is transformed to compound B at a known rate once the ink has been deposited on a writing surface and exposed to the air, a simple quantification of the ratio of A to B can be measured using standard non-destructive analytical techniques, including spectrometry. The elapsed time is then determined from predetermined calibrated time curves. The curves generated are ratio curves which plot the amount of reactant divided by the amount of product, versus time.

The use of a ratio solves the problems associated with measuring raw characteristics. Given that the amount of ink applied to a document is small, the quantity of the ink present is difficult to measure. Further complicating this measurement is the fact that even if the quantity of ink present were destructively measured, such quantity varies with different ink pens and different signers. Some signers write lightly while others bear down. The percentage of a scaler characteristic would therefore be most difficult to ascertain.

However, by computing the ratio of the reactant to the product, the physical amount of ink, or its concentration, is not important. Regardless of whether there are large or small amounts of ink available for analysis, the ratio will be the same for any particular stage of the reaction. Further, the use of a ratio facilitates spectroscopy, a well known non-destructive method of measuring the components present.

Performing a time dating analysis of an ink having time dependent characteristics includes the steps of first measuring the spectral characteristics of the ink in units of percent reflectance and then referring to known reaction rates.

A second embodiment of the present invention relates to the oxidation of compounds in the ink. Oxidation of specific compounds is a well understood process which, under a given set of parameters, including time and reaction rates, can be accurately predicted. Reaction rates can be buffered or modified to give extended or shortened reaction times. Products of the oxidation reactions as well as the amount of reactants remaining may be determined using established spectroscopic or other applicable non-destructive analytical techniques.

DETAILED DESCRIPTION OF THE PREFERRED EMBODIMENTS

Figure 1:
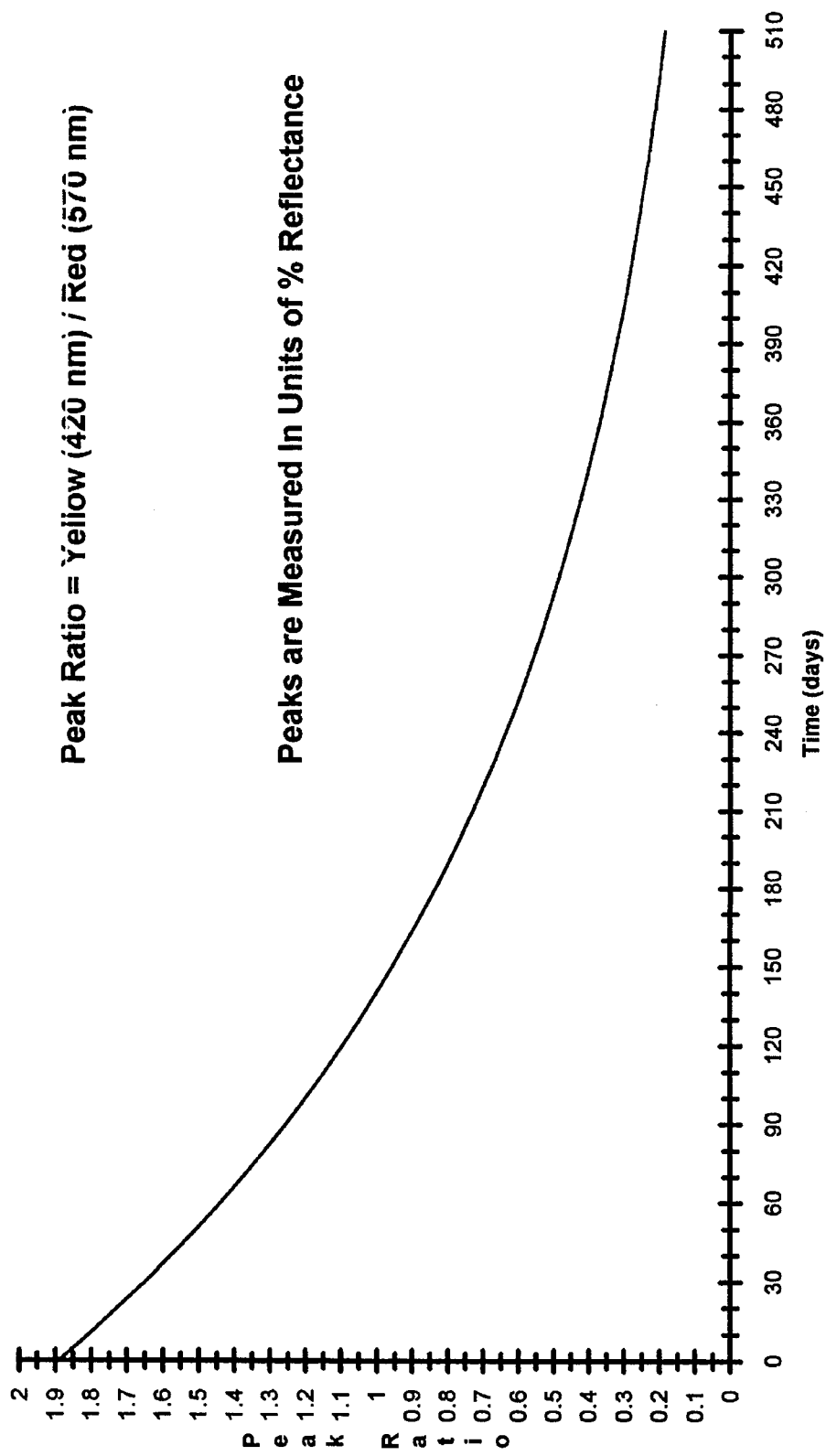
FIG. 1 is a graphical illustration of the peak ratio of yellow light (420 nm) to red light (570 nm) plotted as a function of time in days.

The inks of the present invention include chemical compositions containing active time dating compounds that allow a reliable determination to be made as to the age of a writing. The time dating is accomplished by non-destructively analyzing the composition of the ink by means of spectroscopy, for example. One or more time based chemical mechanisms may be incorporated in a given ink, as desired, in order to enhance the accuracy of the determination being made.

Determining the age of an ink writing that has been deposited on paper has already been studied. Several methods have been applied to time date ink deposited by commercially available pens. Generally, these methods are based on the fact that standard pen ink does not completely dry for several years. Ink that is newer, and therefore less set, dissolves in suitable solvents at a faster rate than ink that is older and dryer. These measurement techniques provide only a general approximation as to the ink age and are destructive to the sample by the very act of dissolving a segment of the writing. This is most undesirable if the writing in question is to be used as evidence in a court of law.

Others have identified specific batches of ink by placing minute amounts of rare earth elements as tracers in the ink. This approach obviously does not provide specific information as to the time history of the ink and relates only to identifying a particular ink used for a particular lot of pens. In addition, due to the large number of ink manufacturers and inks imported from overseas, identifying the time an ink writing was made has become increasingly difficult.

The preferred inks and methods of this invention rely upon the fact that inks can be formulated with compounds having time dependent characteristics that are detectable in the visible light spectrum. The methods embodied herein are shown with regard to a specific chemical formulation, but it is to be understood that such methods are not necessarily limited to the specific compounds noted herein or to the specific type of analysis used herewith.

Other reactive formulations and methods of analysis can be effectively implemented for any portion of the electromagnetic spectrum, including but not limited to ultraviolet, infrared, and so on. Moreover, any quantitative analysis which allows the measurement of reaction products as well as reactants is applicable to the age determination technique described below.

In general, if compound A in the ink is transformed to compound B at an established time rate once the ink has been exposed to air or to evaporation, a simple quantification of the A to B ratio can be measured using standard analytical techniques. The exposure to air occurs after the ink is deposited on a writing surface. The elapsed time after deposition is then determined from calibrated time curves that have been established for the ratios of the compounds selected. The nature of compounds A and B and the specific chemistry of their interactions may be uniquely tailored to provide a desired time base for the analysis.

It may be desirable to add several active compounds to the ink having different, but known, reaction rates depending upon the resolution and the length of time for which the analysis is relevant. An ink deposit containing an active compound whose principal change occurs from 0 to 3 months would usually provide the most accuracy for the short term. In this same regard, it is the earliest portion of the curve in FIGS. 1, 2 and 5 which gives the greatest variation per unit time.

Referring now to FIG. 1 of the drawings, a graph is shown having an ordinate scaled to values of peak ratio, from 0 to 2. A continuous curve is formed as the ratio of the magnitude of yellow light reflected at 420 nm (nanometers) to the magnitude of red light reflected at 570 nm. The advantage of using a ratio, as compared to using the magnitude of a single color, is that a ratio is not dependent upon the amount and thickness of the ink present on the writing surface. A signature characterized by a thick, closely packed area of ink would give a high magnitude of a given color, whereas a signature characterized by a thin, widely spread area of ink would yield a low magnitude of given color. When relative magnitudes are used both of the aforementioned effects are advantageously canceled out.

The abscissa axis (in FIG. 1) extends to a period of 510 days. Note that the change between 30 and 60 days corresponds to a change in the peak ratio from about 1.65 to 1.45, or a difference of about 0.2. A 30 day change from 480 to 510 days results in a peak ratio change of about 0.20 to about 0.16, or a difference of about 0.04. Thus, the longer the passage of time after time zero, the more difficult it is to measure changes in the peak ratio, not only because of the flattening of the curve, but also because of the difficulty to precisely and accurately measure the magnitudes of light reflectance which make up the peak ratio.

Figure 2:
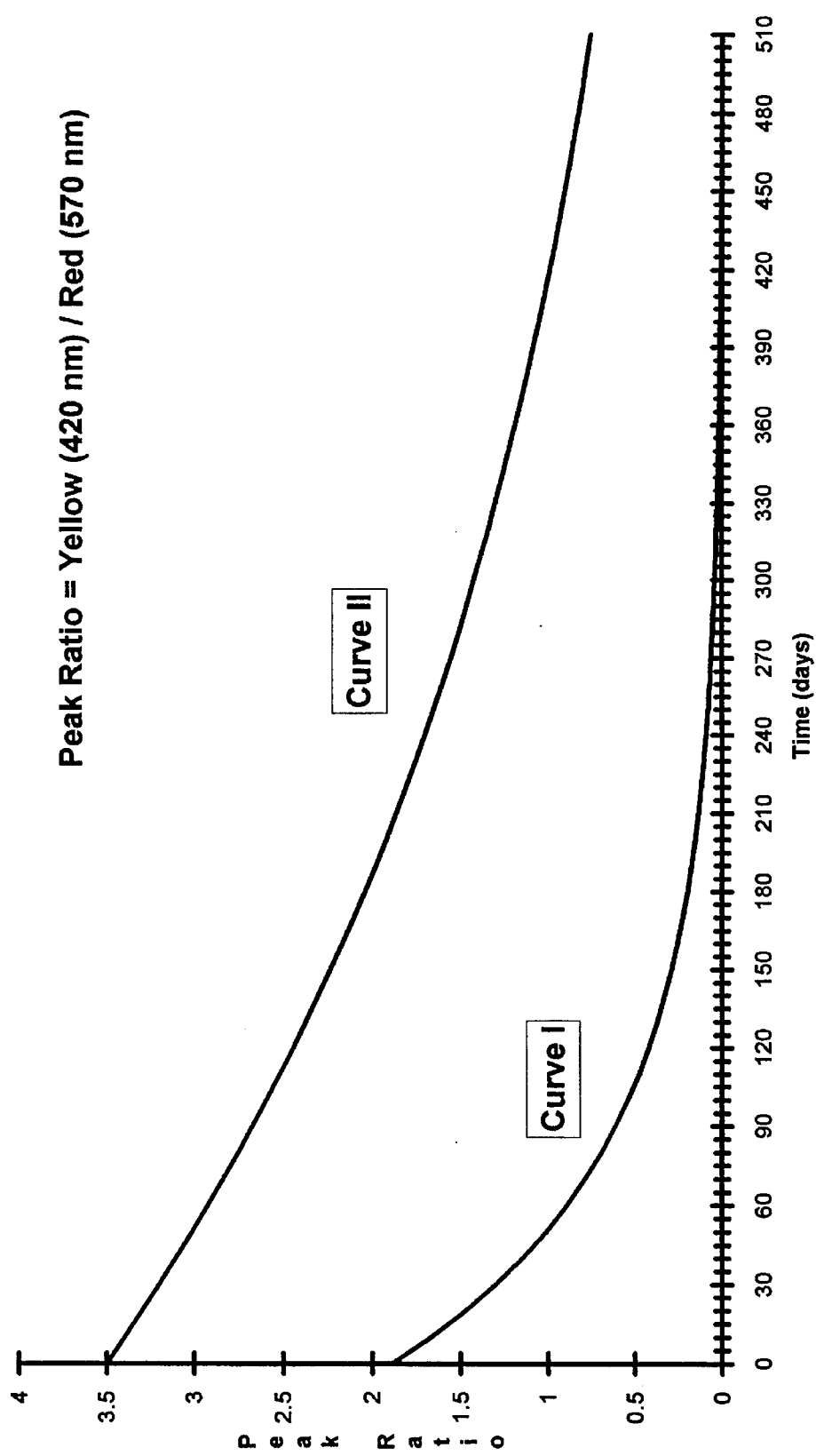
FIG. 2 is a dual line graphical illustration of the peak ratio of yellow light (420 nm) to red light (570 nm) plotted as a function of time in days.

Referring to FIG. 2, a graph is shown illustrating the side-by-side comparison of two reaction curves, designated I and II, having different time rates. Both curves I and II are produced by using the same optical information that produced the ratio for generating the curve of FIG. 1. Curve I has a more rapid decay and is shown asymptotically approaching the abscissa. As can be seen from curve I, if a measurement were made at 360 days, the peak ratio would be very close to zero, just as it would if a measurement were made at 510 days. Curve II, however, has a more gradual rate of decline. Unlike Curve I, Curve II has the ability to provide meaningful time indications from 420 to 500 days.

As described above, there are two mechanisms considered to be practical for determining the time of ink deposition, namely oxidation of the compounds in the ink and pH shifts of the compounds in the ink. Both of these mechanisms, under a given set of circumstances, including time and reaction rates, can be accurately predicted. Reaction rates can be buffered or modified depending upon the time frame or time frames desired to be covered by the analysis. Products of the reactions may be quantitatively determined using established spectroscopic or other applicable analytical techniques.

Mechanism one—pH Shift

The pH mechanism is used to shift the acid/base balance of the ink, thus promoting chemical reaction of some pH sensitive compounds in the ink. Such pH shifts are the result of the evaporation of certain chemicals in the ink, and time dating is therefore achieved after the ink has been exposed to the ambient atmosphere. The rate of shifts in pH levels can be buffered or moderated in the ink composition to facilitate the use of longer and shorter time spans. The resulting change in the ink composition can be measured quantitatively by spectroscopy, or by other methods, including chromatography, and the like.

A specific ink composition will now be disclosed which utilizes a pH based age determining mechanism. This ink includes an indicator dye that has the ability to change color with changes in pH and has the following range of compositions:

| | Range | Preferred |
|---|---|---|
| ethylene glycol monophenyl ether (solvent) | 25%–55% | 28% |
| synthetic resin CA (thickener-binder) | 20%–45% | 28% |
| phenolsulfonphthalein dye (color) | 2%–12% | 7% |
| triethanolamine (pH adjuster) | 10%–40% | 37% |
| | | 100% |

The ink composition listed above is but one example of a variety of possible pH based ink compositions which could be used. This ink has a viscosity of 5,000 to 10,000 centipoise at 25° C. in order to be used in a ballpoint pen.

Figure 3:
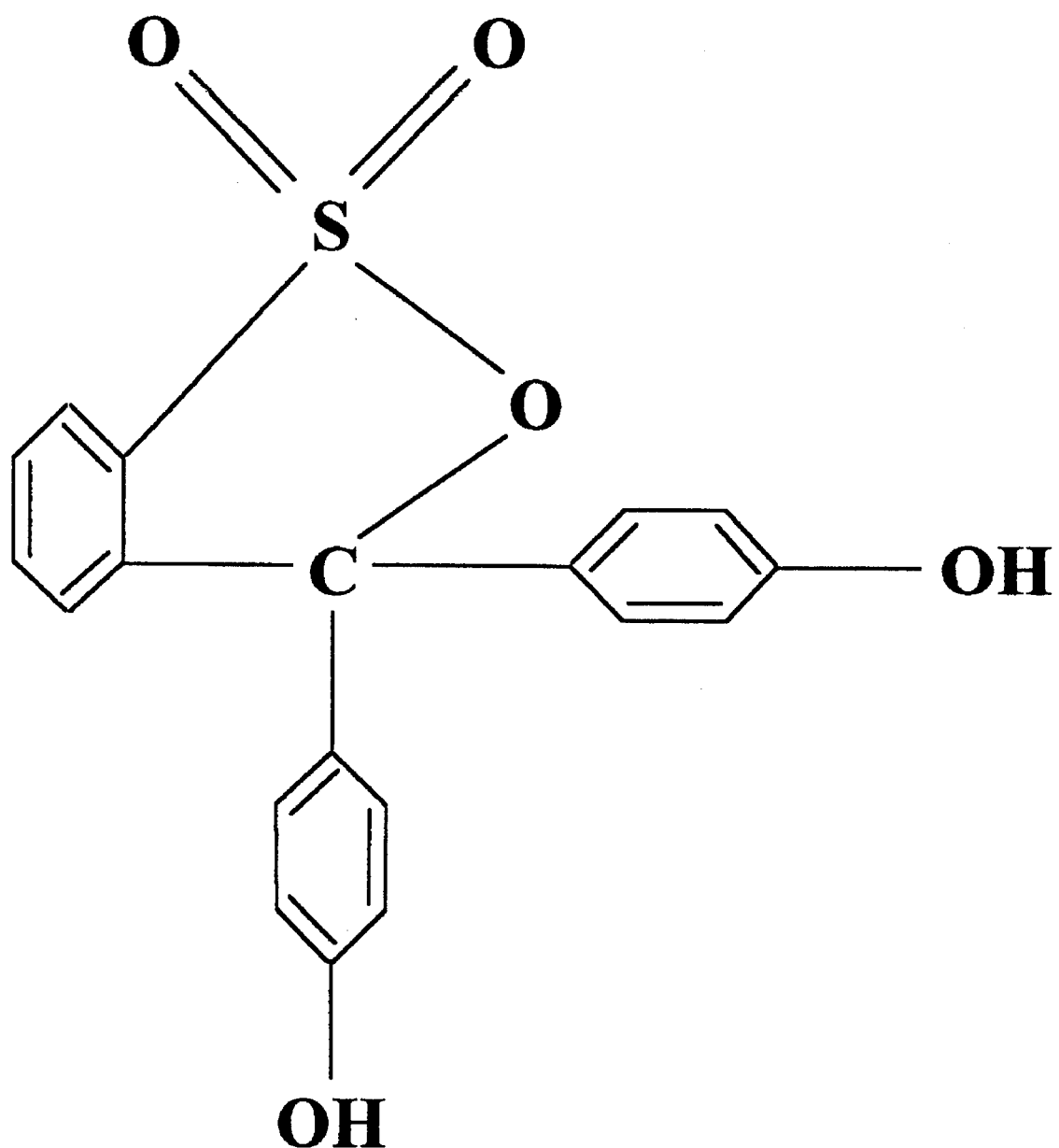
FIG. 3 is a two dimensional representation of $C_{19}H_{14}O_5S$.

The phenolsulfonphthalein dye (phenol red) has a chemical structure which is illustrated in FIG. 3. Above pH 8.4, the dye is bright red, below pH 6.8, the dye is yellow, with the dye having varying shades of orange therebetween. Other dyes which may be used in this invention include: cresol red which has a pH range of 7.2–8.8 and would change from red to yellow, bromthymol blue which has a pH range of 6.2–7.6 and would change from blue to yellow, m-cresol purple which has a pH range of 7.6–9.2 and would change from purple to yellow, and thymol blue which has a pH range of 8.0–9.6 and would change from blue to yellow.

Triethanolamine is an alkaline high-boiling liquid that raises the pH to about 9.0 so as to cause the ink to be red. As long as this ink remains in the pen it is stable and retains its red color. Once deposited on paper, the triethanolamine slowly evaporates, the pH drops, and the ink slowly changes to yellow. This process can take from weeks to months, depending on the exact proportions and ingredients in the formula. Different resins or different amines can be used to speed up or slow down the process.

For example, amines which can be used from fastest acting to slowest, include morpholine, monoethanolamine, diethanolamine, and QUADROL (a complex isopropanol amine commercially available from Wyandotte Chemicals, Inc.). With regard to the amines, it is the evaporation rate thereof which is used to select the speed at which the chemical reaction will occur.

Other resins, in addition to the synthetic resin CA (commercially available from the Huls Company), include the synthetic resins SK and EP-TC (all of the aforementioned are ketone resins), polyvinyl pyrrolidone, JONCRYL 611 (commercially available from Johnson Wax), and ARCAL SAA-100 and SAA-101, a modified polystyrene (available from ARCO Chemical).

Example of other suitable solvents include benzyl alcohol, butylene glycol, propylene glycol, diethylene glycol monoethyl ether, dipropylene glycol, and dipropylene glycol monoethyl ether.

Figure 4:
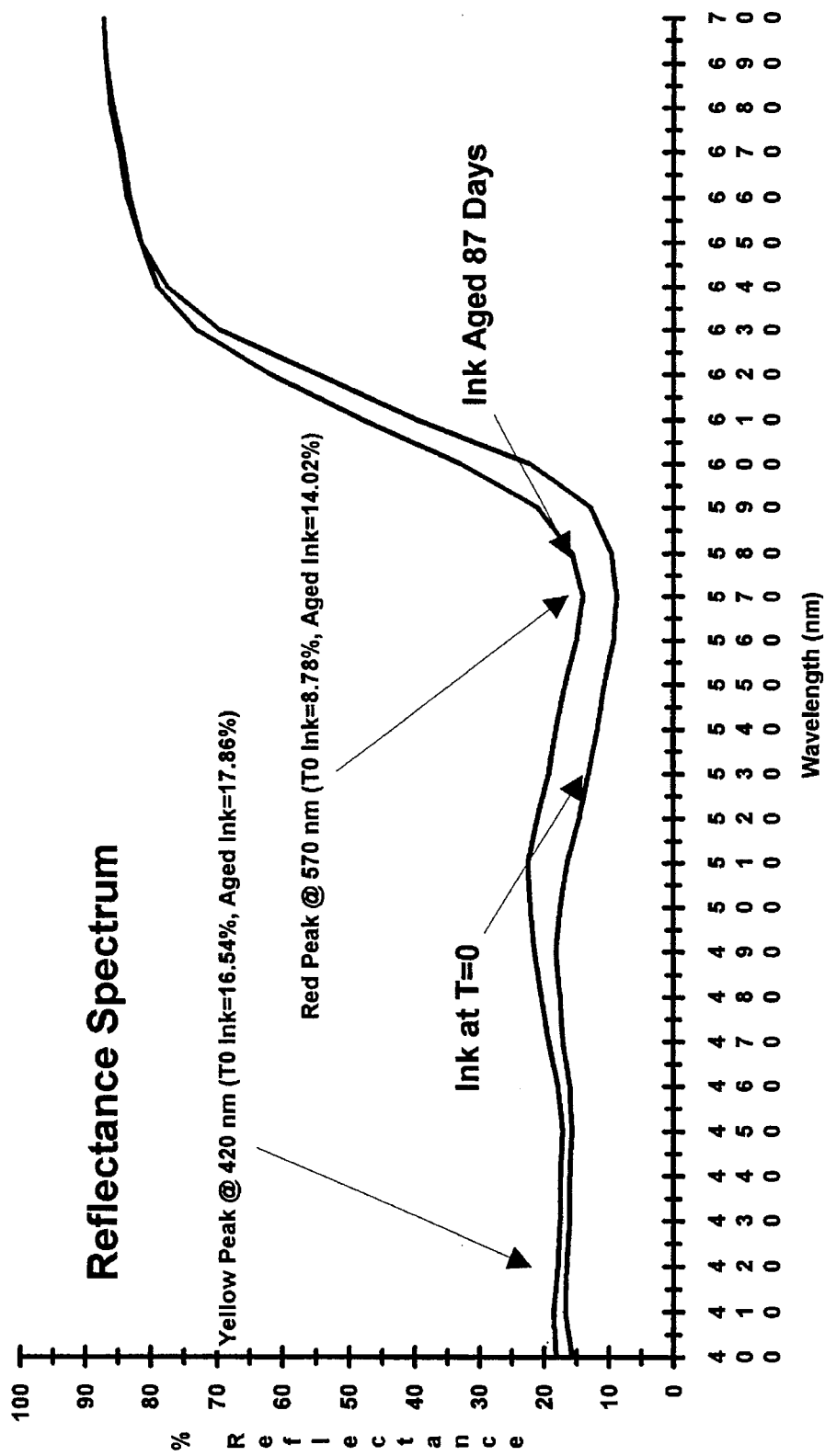
FIG. 4 is a dual line graphical illustration of the reflectance spectrum of yellow light (420 m) and the reflectance spectrum of red light (570 nm), including a first plot for an ink which has just been deposited and a second plot for an ink which was deposited at a different time.

The shift in the characteristics of the ink has been demonstrated experimentally. Referring to FIG. 4, a graph illustrates the visible light spectrum measurements of the preferred ink at time zero and at 87 days after deposition. The data was recorded on a MICROFLASH 200D colorimeter manufactured by Datacolor Inc. The mechanism for color change of the phenol red molecule of FIG. 3 is a change from an OH radical to an $O^-$. The pH range over which the invention is applicable can be as high as a pH of 10, depending upon the amines to be selected for the ink composition, and as low as 6, due to atmospheric $CO_2$ and the evaporation of the amine.

Referring once again to FIG. 4, the ordinate axis of the graph represents percent reflectance. The graph illustrated in FIG. 4 is not time based, but shows a sweep of a sample of the ink across the visible electromagnetic spectrum. The percent reflectance indicates the percentage of light reflected (or absorbed) at a given frequency. Thus, 100% reflectance indicates no absorption of the electromagnetic energy by the ink, while 0% reflectance indicates that all of the energy was absorbed.

The plot of FIG. 4 labelled by the indicia reading "Ink at T=0" is the reflectance spectrum of the ink when it is initially deposited on paper. Also, the plot labeled by the indicia reading "Ink Aged 87 Days" represents the reflectance spectrum of the ink eighty seven days after deposition. The measurements derived from the plots of FIG. 4 are used to construct the plots shown in FIGS. 1, 2, 5 and 6.

Of the entire electromagnetic spectrum shown in FIG. 4, the frequencies corresponding to a yellow wavelength of 420 nm and to a red wavelength of 570 nm were selected to construct the aging plots. Referring to the plot labeled "Ink at T=0," the ink will initially be characterized by a reflectance of yellow light at 16.54% and a reflectance of red light at 8.78% to yield a peak ratio of about 1.88. As is also shown in FIG. 4, and referring to the plot labeled "Ink at T=87 days," the ink is now characterized by a reflectance of yellow light a 17.86% and a reflectance of red light at 14.02% to yield a peak ratio of about 1.27.

Figure 5:
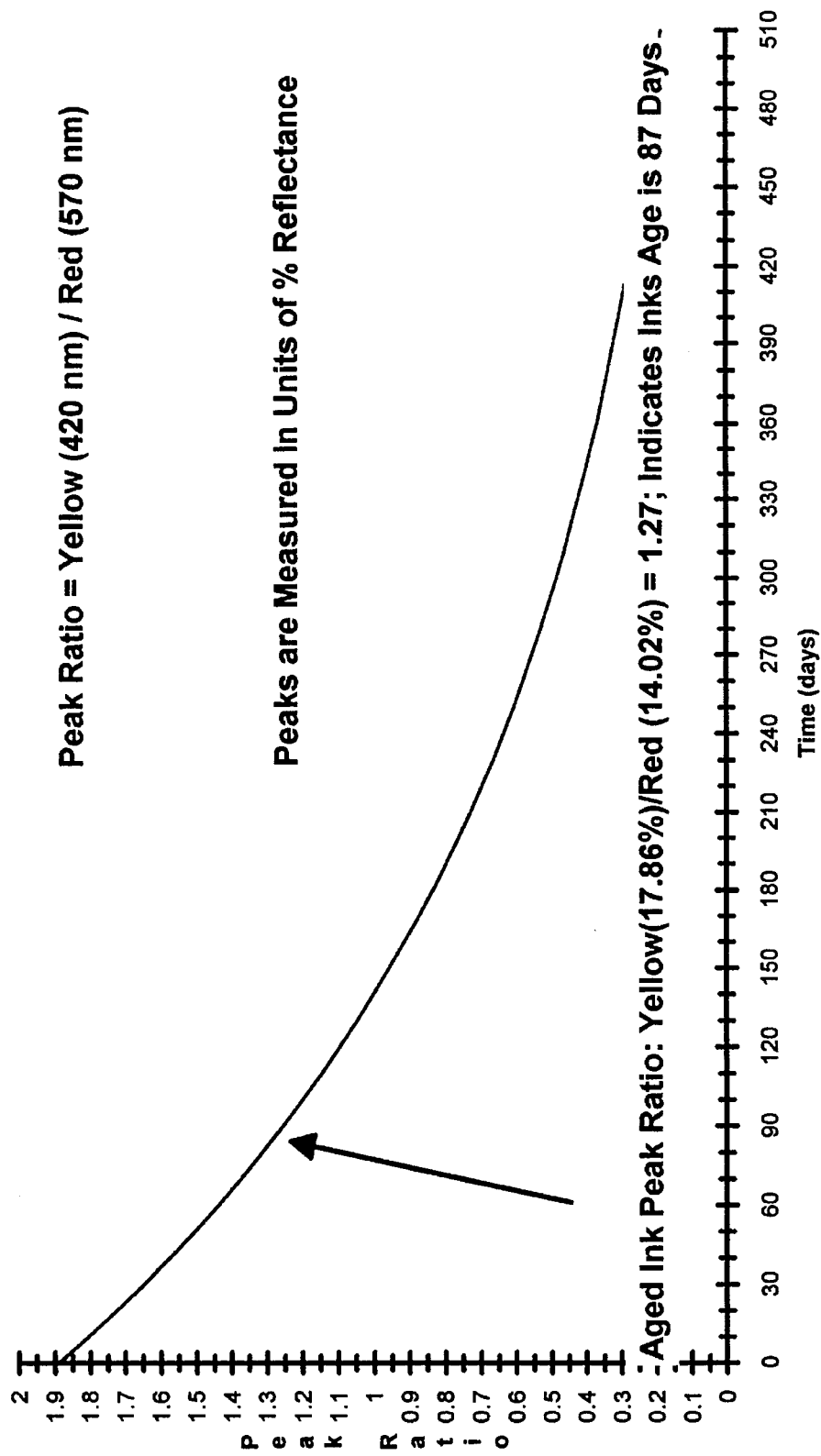
FIG. 5 is a specifically scaled graphical illustration of the peak ratio of yellow light (420 nm) to red light (570 nm) plotted as a function of time in days which corresponds to the plot of FIG. 4.

Referring to FIG. 5, the use of these two peak ratio calculations is shown for determining elapsed time. The peak ratio of 1.88 obtained just after the ink was first deposited corresponds to a time of zero. The peak ratio of 1.27 obtained long after the ink was deposited corresponds to a time of eighty seven days.

Since the ink was formulated to change spectrally when exposed to the ambient atmosphere, two specific wavelengths of light were chosen to be measured in order to quantify that change, and the ratios of the two peaks were calculated to determine the time elapsed or aging after deposition. As the pH decreases, the color of the ink changes from red to yellow, and thus the spectral wavelengths selected for this ratio were the 420 nm yellow wavelength and the 570 nm red wavelength. As shown in FIG. 5, by dividing the percent of spectral reflectance of the yellow wavelength by the percent of spectral reflectance of the red wavelength, it is possible to accurately identify the age of the ink after it has been deposited on a writing surface. The curve in FIG. 5 is specific to a particular ink formulation and will vary, as mentioned above, with changes in the composition of the ink.

Figure 6:
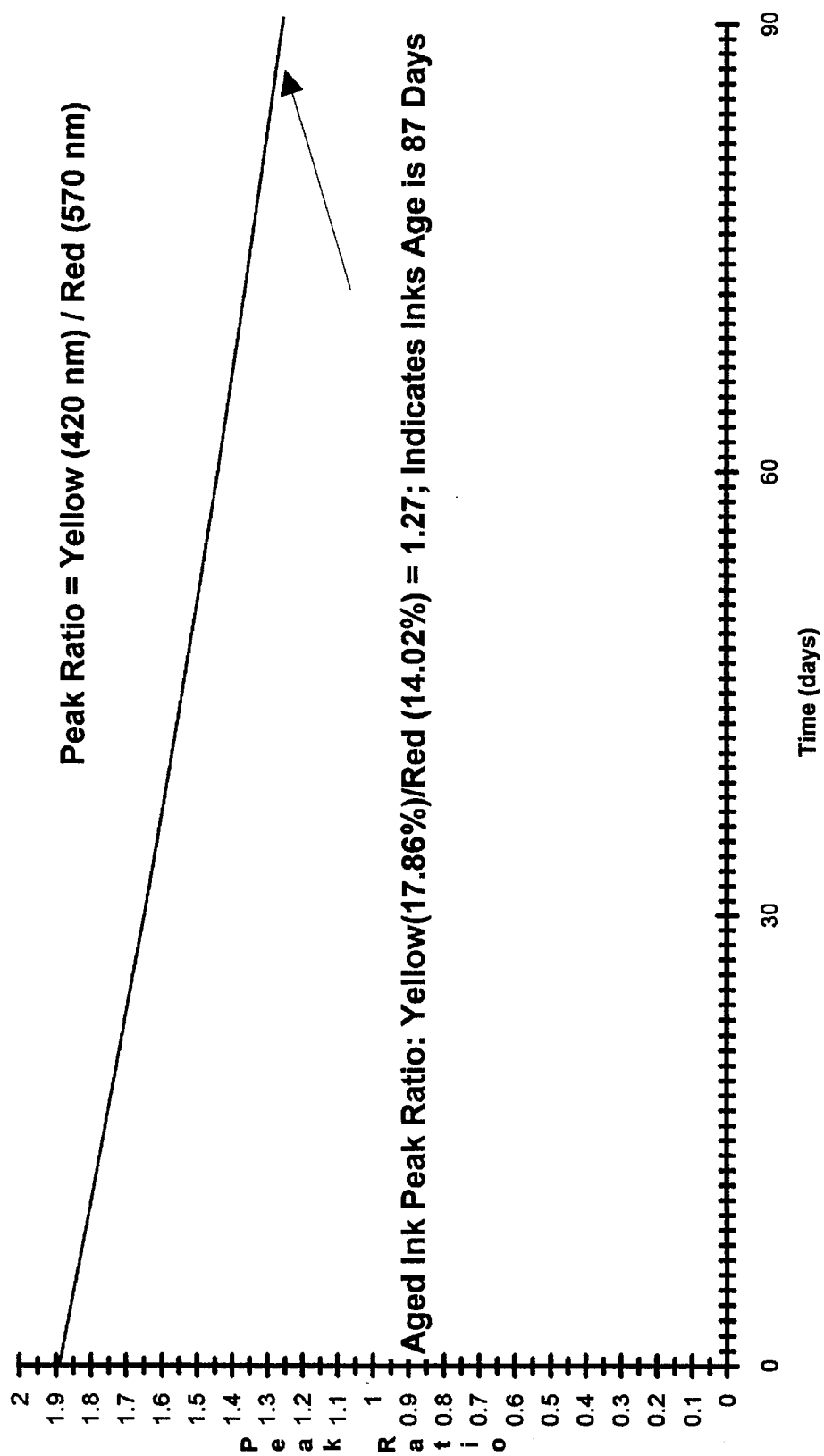
FIG. 6 is a graphical illustration that is similar to the illustration shown in FIG. 5 except that the time parameter has been limited to 90 days.

Referring to FIG. 6, a curve is shown which is similar to that of FIG. 5. However, the time (i.e. abscissa) axis has been adjusted to show only the first ninety days after T=0, and the time scale increments have been modified to show one day intervals. At this scale, the 1.27 peak ratio computed earlier coincides with the same eighty seven day old ink that was identified by using the plot of FIG. 5.

Mechanism Two—Oxidation

An oxidation based method according to the present invention for determining the age of an ink involves the use of certain dyes which have varying degrees of instability and which will slowly lose their color or fade over time due to oxidation. These unstable dyes are used in conjunction with stable dyes which fade extremely slowly. An example of an unstable dye is the magenta colored rhodamine B base (color index number solvent red 49). An example of a stable dye is the cyan colored solvent soluble copper phthalocyanine (solvent blue 38). The two dyes mentioned above are used in the ink composition listed below and produce an ink which is violet in color. The fading of the unstable dye, rhodamine B, will cause the violet color of the writing to slowly turn to cyan, the color of the stable dye. A preferred composition is as follows:

|  | Range | Preferred |
| --- | --- | --- |
| ethylene glycol monophenyl ether | 45%–55% | 48% |
| synthetic resin CA | 10%–35% | 25% |
| rhodamine B base (solvent red 49) | 2%–10% | 5% |
| solvent soluble copper phthalocyanine (solvent blue 38) | 10%–30% | 20% |
| oleic acid | 1%–5% | 2% |
|  |  | 100% |

The oleic acid, a fatty acid with 18 carbon atoms, is provided to solubilize the dyes and adjust the pH, which should be close to neutral (a pH of 7.0). The viscosity of the resulting ink will be between 5,000 and 10,000 centipoise at 25° C. for use in a ballpoint pen. The dye number references listed above are in accordance with the Color Index established by the American Association of Textile Chemists and is an industry standard. The above composition will react over a period of years instead of months to give a long range time base. However, it is possible to substitute more resin to yield a longer time period and less resin for a faster reaction. However, the total amount of resin which can be added is constrained by the viscosity of the resulting ink.

Again, this ink is stable as long as it is contained in a pen cartridge, but the rhodamine B base will start to fade from magenta to colorless as soon as it is deposited on paper. The solvent soluble copper phthalocyanine will remain a stable cyan color. Each of the two dyes will have its own colorimetric absorption peak, and the ratio of the magnitudes of these two peaks can be measured with an electronic colorimeter and is proportional to the age of the ink after deposition. It is to be noted that the ratio computed immediately after the ink is deposited will always be the same, inasmuch as it is fixed by the ink composition and is independent of the amount of ink deposited on the paper.

As was the case for the pH change ink, different solvents and resins can be substituted. As was earlier disclosed, other resins include synthetic resin SK, EP-TC, polyvinyl pyrrolidone, JONCRYL 611 and the ARCAL resins. Examples of other solvents include benzyl alcohol, butylene glycol, propylene glycol, diethylene glycol monoethyl ether, dipropylene glycol, and dipropylene glycol monoethyl ether.

Other dyes are also utilizable as substitutes in the above composition. The unstable dye rhodamine can be replaced by such unstable dyes such as methyl violet base (solvent violet 8) and victoria blue B base, both of which change gradually from purple and blue, respectively, to colorless.

The more stable solvent soluble copper phthalocyanine can be replaced by Neozapon Yellow R, a dye which is commercially available from BASF, or by Orasol Red G, a dye which is commercially available from Ciba Geigy.

While the present invention has been described in terms of a composition of ink and a method of measuring the characteristics of an ink deposit to determine the elapsed time after deposition, one skilled in the art will realize that the formulations and techniques of the present invention can be applied to many processes and compounds. More particularly, and with regard to the pH shift mechanism described above, it is within the scope of this invention to reverse the process of detecting the pH shifts going from low to high instead of from high to low by means of adding to the ink an acid that is susceptible to evaporation after deposition. It is also within the scope of this invention to automate the graphical methods with respect to the pH shift mechanism illustrated in FIGS. 4–6 by making mathematical computations with the aid of a computer.

Although the invention has been derived with reference to particular illustrative embodiments thereof, many changes and modifications of the invention may become apparent to those skilled in the art without departing from the spirit and scope of the invention. Therefore, included herein are all such changes and modifications as may reasonably and properly be included within the scope of this contribution to the art.

We claim:

1. A method for determining the age of ink deposited on a writing surface, said method comprising the steps of:

measuring the amount of light at a first wavelength that is reflected from the ink at a first time after the ink has been deposited on the writing surface;

measuring the amount of light at a second wavelength that is reflected from the ink at said first time;

computing a first ratio of the amount of light reflected from the ink at said first time at each of the first and second wavelengths;

measuring the amount of light at the first wavelength that is reflected from the ink at a second time after the ink has been deposited on the writing surface;

measuring the amount of light at the second wavelength that is reflected from the ink at said second time;

computing a second ratio of the amount of light reflected from the ink at said second time at each of said first and second wavelengths; and comparing said first and second ratios to one another, such that the respective magnitudes of said first and second ratios indicates the age of the ink between said first and second times.

2. The method recited in claim 1 including the additional step of spectroscopically measuring the amount of light at said first and second wavelengths that is reflected from the ink at said first and second times.

3. The method recited in claim 1 including the additional step of adding to the ink to be deposited on the writing surface a chemical which is susceptible to oxidation when exposed to the air for causing the color of said ink to change between said first and second times.

4. The method recited in claim 1 including the additional step of adding to the ink to be deposited on the writing surface a chemical which is susceptible to a pH change when exposed to the air for causing the color of said ink to change between said first and second times.

* * * * *